United States Patent [19]

Liedholz

[11] Patent Number: 4,580,096
[45] Date of Patent: Apr. 1, 1986

[54] ISOTACHOPHORESIS ANALYZER FOR INDUCTIVELY DETECTING BOUNDARIES BETWEEN ADJOINING SUBSTANCES HAVING DIFFERENT CONDUCTIVITIES

[75] Inventor: Gerhard A. Liedholz, Miami, Fla.
[73] Assignee: Coulter Electronics, Inc., Hialeah, Fla.
[21] Appl. No.: 280,409
[22] Filed: Jul. 6, 1981
[51] Int. Cl.⁴ ............... G01N 27/74; G01R 33/12
[52] U.S. Cl. ................... 324/204; 324/234; 324/445
[58] Field of Search ........ 324/204, 228, 234, 236–243, 324/71.1, 71.4, 445; 336/30, 180, 181

[56] References Cited

U.S. PATENT DOCUMENTS

| | | | |
|---|---|---|---|
| 2,435,043 | 1/1948 | Lehde et al. | 73/194 |
| 2,542,057 | 2/1951 | Relis | 175/183 |
| 2,625,588 | 1/1953 | Peters | 324/445 |
| 2,652,925 | 9/1953 | Vermeiren | 336/180 |
| 2,656,508 | 10/1953 | Coulter | 324/71 |
| 3,502,974 | 3/1970 | Coulter et al. | 324/71 |
| 3,924,180 | 12/1975 | Salzman et al. | 324/71.1 |
| 3,942,105 | 3/1976 | Bondarenko et al. | 324/234 |
| 3,987,362 | 10/1976 | McCann et al. | 324/30 A |
| 4,027,233 | 5/1977 | Shmakov et al. | 324/204 |
| 4,187,462 | 2/1980 | Haker et al. | 324/204 |

OTHER PUBLICATIONS

Alder et al., "A Non-Intrusive Very High-Frequency Conductivity Detector for Continuous Flow Monitoring", Analytica Chimica Acta, 110 (1979) pp. 325–328.
"Principles and Applications of Isotachophoresis", by Yutaka Nagayanagi, American Laboratory, Oct. 1977, pp. 101–107.

Primary Examiner—Gerard R. Strecker
Assistant Examiner—Walter E. Snow
Attorney, Agent, or Firm—Stephen A. Roen; Gerald R. Hibnick

[57] ABSTRACT

Disclosed is an inductance detector for detecting boundaries between and characteristics of at least two adjoining substances having different characteristics, such as impedance, wherein a coil assembly, which is energized by an alternating current, is electrically coupled to a detector for detecting at least changes in impedance of the coil assembly caused by the boundary proceeding into and through the coil assembly.

32 Claims, 7 Drawing Figures

ISOTACHOPHORESIS ANALYZER FOR INDUCTIVELY DETECTING BOUNDARIES BETWEEN ADJOINING SUBSTANCES HAVING DIFFERENT CONDUCTIVITIES

FIELD OF THE INVENTION

The invention is related to detector devices for detecting the passing of a boundary of two adjoining substances having differing characteristics.

DESCRIPTION OF THE PRIOR ART

In the art area of isotachophoresis, an ion sample in a capillary tube, having one or two supporting electrolytes, is separated into zones. Each zone contains one component ion of the ion sample and the order of the zones is determined by the mobilities of the component ions. Moving boundaries between adjoining zones have in the prior art devices been typically detected by three types of detectors: thermometric, ultraviolet absorption and potential gradient, as described in an article entitled "Principles and Applications of Isotachophoresis", by Yutaka Nagayanagi, AMERICAN LABORATORY, October 1977, pp. 101-107. The thermometric detector consists of a small thermocouple or thermistor attached to the wall of the capillary tube that responds to the temperatures of the zones. The UV-absorption detector determines the passing of a boundary by the change of the amount of UV absorption between the zones. The potential gradient detector consists of two small, closely spaced electrodes that detect the potential between them, which is proportional to the resistivity of a zone. Depending upon the sample fluid being processed, all three of these detection methods for detecting moving boundaries have some disadvantages. The thermometric detector has relatively low resolution and sensitivity. The UV-absorption detector requires an electro-optical system and UV-absorptive zones. The potential gradient detector electrodes contact the fluid and therefore are subject to electro-chemical artifacts. Further, the electrodes can be at a very high voltage, thus requiring adequate HV insulation and a system for translating the electrode voltage difference to near ground level.

In other art areas, measurements of the electrical conductivity of a stationary liquid by a magnetic field have been made. In U.S. Pat. No. 2,542,057 to Relis a pair of coils are immersed in a liquid for determining its conductivity. An alternating current in the first coil sets up a magnetic field to induce a voltage in the second coil, the induced voltage being a function of the fluid conductivity.

U.S. Pat. No. 2,435,043 to LEHDE et al. discloses a speed measuring device wherein a pair of outer coils are energized by an A.C. source in such a manner that their magnetic effects oppose each other. A third detector coil is positioned midway between the two outer coils so that when there is no fluid flow around the housing, there is no voltage induced in the detector coil. With the flow of the fluid, a voltage is generated in the detector coil. The magnitude of this voltage is a function of the speed of the fluid.

U.S. Pat. No. 3,987,362 to McCann et al. teaches the use of consecutive energized and nonenergized coils for determining the conductivity of a conductive fluid flowing on the outside of the coils to monitor the temperature and flow rate of the liquid.

SUMMARY OF THE INVENTION

The invention is directed toward an inductance detector device for detecting boundaries between and characteristics of adjoining substances, including gases, liquids, solids and combinations thereof, having different identifying characteristics, such as admittance or impedance. The inductance detector device comprises a coil assembly which has at least one coil energized by an alternating current which generates eddy currents in the substance. Means are provided for creating relative movement between the coil or coils and the adjoining substances so that the boundaries pass through the coil or coils, thereby causing changes in induced voltages and/or terminal impedance of the coil or coils. The coil assembly is coupled to a detector for detecting these changes and therefore the passing boundaries.

In one embodiment of the inductance detector, a pair of outer coils are disposed around at least one inner coil, with each outer coil having coil turns or coil currents in the opposite direction to the coil turns or coil currents, respectively, of the adjacent inner coil. Hence, the magnetic field created by one or more inner coils away from the center of the assembly is substantially cancelled or reduced, thereby giving better boundary signal resolution.

In another embodiment of the inductance detector, two side-by-side coils, each preferably with substantially the same number of coil turns, have their respective coil turns or coil currents in the opposite direction with respect to each other, so as to provide a region of substantially zero magnetic field intensity therebetween. As a relatively narrow boundary passes through this region, momentarily, the detector will not substantially change its response. Hence, time markers can be readily provided as to the location of a passing boundary. Additionally, field limiting coils can be provided.

In a particularilly desirable application for the inductance detector, the coils of the inductance detector device are wrapped about a capillary tube used for separating a fluid sample in isotachophoresis. Additionally, a coaxially disposed cooling tube can be positioned inside the capillary tube for removing heat. Also, the inductance detector can be used in combination with a second detector for sensing magnetic and/or other properties of the fluid sample. In this isotachophoresis application of the inductance detector, the inductance detector is used to detect moving boundaries between adjoining ion components.

The sample flow through the ambit of the coils of the inductance detector effectively forms a single turn coil positioned within the interior confines of the coils wherein relatively concentric eddy currents are induced by the applied A.C. current to the coils. By having opposed magnetic fields generated by adjacent coils, a region of zero magnetic field intensity can be generated therebetween, as previously described. As the boundary between two adjoining substances, which defines two regions of differing impedances, successively traverses consecutive eddy currents, the impedance of the paths of the eddy currents, and therefore their magnitude, increase or decrease, depending upon the respective impedances of the adjoining substances. Changes in the eddy currents can be detected in one of two ways. The variation in the magnitude of the eddy currents will vary the back voltage induced in the energizing coils, which can be detected by impedance variations of those coils. Alternatively, there will be field shifting, primarily caused by the relative rearrangement of the magnetic fields, which can be detected by an inductively energized detector coil positioned between the two opposing energized coils. Additionally, better resolution of the detected signal can be achieved by using the previously described pair of outer coils.

BRIEF DESCRIPTION OF THE DRAWINGS

Further objects and advantages of the present invention will become apparent as the following description proceeds, taken in conjunction with the accompanying drawings in which.

DESCRIPTION OF THE PREFERRED EMBODIMENT

Figures 1, 2:
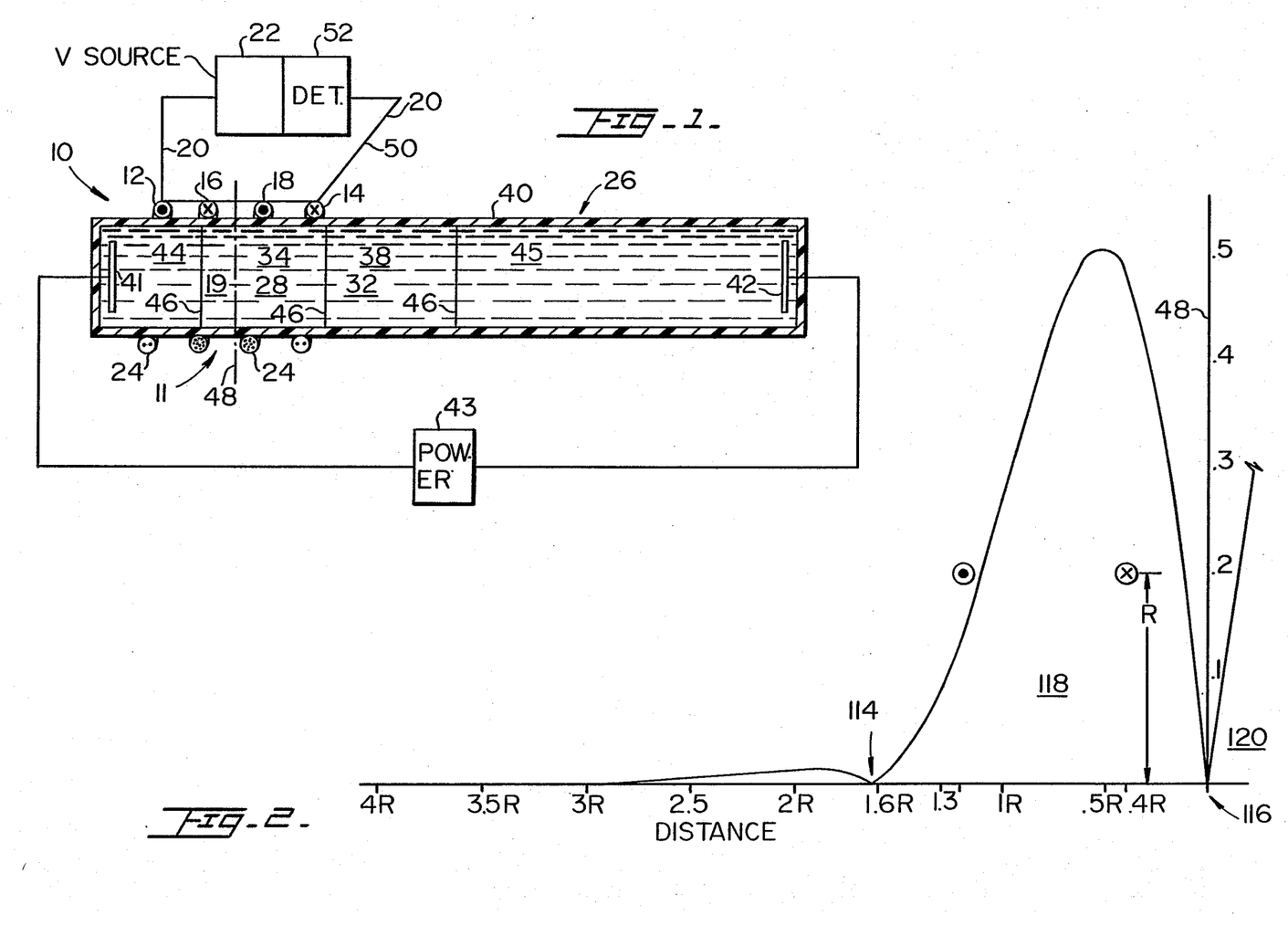
FIG. 1 is a cross-sectional view of the inductance detector.
FIG. 2 is a graph of the magnetic field strength of the inductance detector of FIG. 1.

Referring to FIG. 1, there is disclosed an inductance detector, generally indicated by numeral 10, for detecting the passing of a boundary between at least two adjoining substances having differing characteristics, such as impedance. Additionally, the identity and characteristics of one or both of the two adjoining substances can be detected. The substances can be gases, liquids, solids or some combination thereof. In the preferred embodiment, the inductance detector 10 includes a coil assembly 11 having an outer pair of oppositely wound coils 12 and 14 and an inner pair of oppositely wound coils 16 and 18. Directions of current in coil turns are shown by conventional polarity signs in the drawings. The coils are preferably, but not necessarily, formed from a single wire 20, so that each coil is in series with a voltage source 22. As an example, two circular coil turns 24 of the wire 20 form the coils 12 and 14 and ten circular coil turns 24 form the coils 16 and 18. Preferably, but not necessary, coils 12 and 14 have the same number of coil turns. Each successive coil is wound in opposite directions; hence the coils 12 and 18 are, for example, wound clockwise, while the coils 14 and 16 are wound counterclockwise or vice-versa. The voltage source 22 energizes the coil turns 24 of assembly 11 with a high frequency A.C. voltage. As will become apparent hereinafter, the inductance detector 10 can have other winding and connection arrangements. Moreover, the coil assembly 11, instead of being made from the single wire 20, can be made from a plurality of wires of different sizes. Also, the coil turns 24 can be printed circuit coils of a conventional design.

In one implementation of the inductance detector 10, the detector 10 is used in combination with a well known isotachophoresis arrangement 26. In isotachophoresis, the cationic or anionic ions of a sample are separated into zones between two supporting electrolytes. For the purposes of illustration, an ion sample, having two component ions 28, and 32, is shown already separated into two zones 34, and 38. The other or counter ions of opposite polarity, i.e., the Cl of, e.g., HCl, NaCl, KCl and LiCl, are not shown proceeding in the opposite direction to the co-ions, which in these illustrative examples would be the cations H, Na, K, and Li. The ion sample is introduced into a capillary tube 40, which has a pair of opposed electrodes 41 and 42 mounted at each end thereof. The electrodes 41 and 42 are electrically coupled to a DC power source 43. A pair of electrolytes are used, a first electrolyte 44 or leader, containing a cation that has the highest mobility of all of the cations and a second electrolyte 45 containing a terminating cation which has the lowest mobility of all the cations. The ion sample is injected or placed between the two electrolytes 44 and 45. In FIG. 1, the sample ions to be separated have proceeded toward the oppositely charged electrode 41 so that the sample has separated into the two illustrative zones 34 and 38.

In the above described isotachophoresis environment, the inductance detector 10 is used to detect moving boundaries 46 of each zone. This isotachophoresis application is merely illustrative of one of a number of applications for the inductance detector 10. The inductance detector 10 creates a magnetic field, part of which is contained within the capillary tube 40. As will be described hereinafter, some of the coils are preferably used to focus or concentrate the magnetic field about a center plane 48, which is defined as traversing the capillary tube 40. Connected in a connecting circuit 50 with the A.C. source 22, is a detector 52. Although the coils of the coil assembly 11 are shown in series with the A.C. source 22 and the detector 52, numerous other connecting circuits 50 are possible, such as, for example, a parallel circuit arrangement. Various other connecting circuit arrangements will be illustrated hereinafter. The detector 52 is of a conventional type capable of detecting changes in the impedance of the coil assembly 11. Typically, the A.C. source 22 and the detector 52 are combined in a single, conventional oscillator detector designed to respond to resistive and/or frequency changes caused by impedance changes of the ion sample. The oscillator detector can be one of several well known types in the art of electrical measurements, such as a well known marginal oscillator, which is disclosed in U.S. Pat. No. 4,208,624 to Miller and in an article entitled "A High Field Nuclear Magnetic Resonance Probe Using Transistors", *Journal of Scientific Instruments*, by F. N. H. Robinson, 1965, Volume 42. The marginal oscillator typically has a capacitor element which, in combination with the inductance of the coil assembly 11, results in resonance at some desired frequency. As one of the moving boundaries 46 approaches and passes through the center plane 48, the magnetic field, generated by the inductance detector 10, is modulated so that the current and/or voltage received by the detector 52 varies accordingly. The different component ions normally have different conductivities. One manner of illustrating the impact of varying conductivities on the current and voltage of the circuit 50 is to consider the circuit 50 as a primary circuit of a transformer and the sample liquid as an equivalent secondary circuit of the transformer with a variable load. Hence, the real component of the variable load, the resistance, will vary in magnitude with the conductivity of the component ion. Continuing the analogy, through the mutual inductance of the primary and secondary circuits, a variation of the conductivity of the ion sample correspondingly modifies the impedance of the circuit 50, such signal variation being subsequently detected by the detector 52. In actuality, the greater the conductivity of the zone, the greater the magnitude of the eddy current generated in the zone and therefore the greater power loss, or to put it another way, the less the impedance of the coils. This change in impedance results in a change in current and/or voltage of the circuit 50. The order of the zones, each of which contain only one component co-ion, is determined by the respective mobilities of the component ions. Moreover, the measurements of the lengths of each zone, as accomplished by detecting the boundary between each zone, give quantities of component ions contained in the ion sample. Not only does the change in detected impedance indicate a boundary and its location, but the magnitude of the detected impedances can be used to identify the ion components.

In the preferred embodiment of FIG. 1, a multiple coil arrangement for the coil assembly 11 is shown. However, in the broadest scope of the invention, a single coil of wound wire would achieve the desired objective of detecting a boundary between differing materials, but with less resolution than the multiple coil arrangement. In the preferred embodiment, the capillary tube 40 is typically 200 to 500 mm long, with 0.5 mm inside diameter. To maximize the field coupling to the fluids, the inside diameter of the coil turns 24 is minimized by having the capillary tube 40 with thin walls, such as 0.05 to 0.1 mm thick. To maximize the resolution, the diameter of the wire 20 is minimized, preferably to 0.025 to 0.050 mm, and the coils' widths, with respect to the longitudinal axis of the capillary tube 40, are minimized by making the coils no more than one or two wire diameters wide. With the four coil arrangement of FIG. 1, the coils 12 and 14 are preferably separated by a distance equal to 2.4 times the radius of the coils and the coils 16 and 18 are separated by a distance equal to 0.8 times the radius of the coils. The coils of each pair of coils are equally spaced from the center axis 48.

The coil assembly 11 is energized by a relatively high frequency alternating current. Frequencies from 10 to 100's of megahertz are usable with the relatively small coils of the coil assembly 11. The effect of the conductivity of the ion sample on the impedance of the coil assembly 11 is increased by increasing the frequency.

Referring to FIG. 2, a graphical representation of the absolute axial magnetic field strength H is shown as a function of axial displacement from one side of the center plane 48. With respect to field strength in a plane passing through the axial center of the coil assembly 11, the absolute strength of the field defines a pair of mirror image sensing zones. However, the two sensing zones have magnetic fields of opposite polarity. Additionally, the coils of the coil assembly 11 are shown in their respective positions. With any arrangement of the coil assembly 11, it is desirable to have two outside coils, such as the outer coils 12 and 14, to substantially cancel or reduce the far ends of the magnetic field. More specifically, in the graph of FIG. 2, the magnetic field strength is substantially reduced from 1.6 radii (R) outward. Hence, this allows the magnetic field to be concentrated or focused with respect to the center plane 48. Generally, these outer coils 12 and 14 have less turns than the inner coils. In summary, the use of the outer coils 12 and 14 reduces the axial length of the sensing field; thereby increasing the resolution detecting of a moving boundary.

Referring to FIG. 2, the winding of the coils 16 and 18 in opposite directions results in a field strength of approximately zero at the center plane 48. As the boundary 46 moves through the mirror image sensing zones of the coil assembly 11, the initially constant impedance signal received by the detector 52 will change, except when the boundary 46 is at the center plane 48, until the boundary 46 has entirely passed through the sensing zones, at which time a new, substantially constant impedance signal is reached. As the moving boundary 46 proceeds axially along the capillary tube 40, in the sensing zones, the rate of change of the impedance signal (current or voltage fluctuation) received by the detector 52 will generally vary with the magnitude of the field strength existing at the instantaneous position of the moving boundary 46. With the field configuration of FIG. 2, the greatest signal fluctuation would occur at a distance of about 0.5R from either side of the center plane 48, while virtually no signal variation occurs in the vicinity of the center plane 48. This reduced signal response area provides a convenient benchmark for determining the location of the moving boundary. In other words, as the boundary 46 proceeds toward the center plane 48, the signal variation increases, then begins to decrease as the boundary approaches the center plane 48, is substantially zero when the boundary is in the immediate vicinity of the center plane 48, and then increases as the boundary moves away from the center plane 48. Measuring the point in time when the boundary passes through the center plane 48 provides particularly reliable data due to the ease required to detect a no signal variation between two peak signal variations. In the broad sense of the invention, the coil assemby 11 can be designed to provide regions of flux absence or variations so as to provide boundary position time markers in the signal variations received by the detector 52. These markers can be used by the electronic circuitry of the detector 52 to provide sample quantity related outputs.

Figure 3:
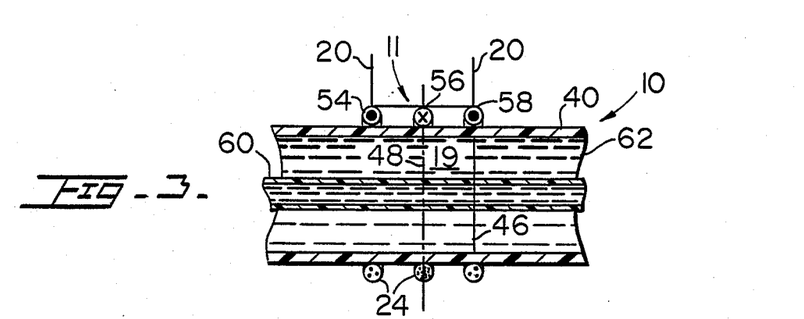
FIG. 3 is a fragmentary, cross-sectional view of a modification to the inductance detector.

FIG. 3 illustrates an alternative embodiment of the inductance detector 10 wherein the wire 20 of the coil assembly 11 is wound into three coils 54, 56, 58. The two outer coils 54 and 58, each preferably with three coil turns 24, are wound in the same direction and the inner coil 56, with preferably twelve coil turns 24, is wound in the opposite direction. The two coils 54 and 58, as undertaken in the first embodiment, act to substantially reduce or cancel the far ends of the magnetic field. The inner coil 56 provides a magnetic field that has its peaked strength in the vicinity of the center plane 48. Consequently, as the moving boundary 46 approaches the center plane 48, the signal variation increases, peaks when the moving boundary reaches the center plane 48 and decreases as the moving boundary proceeds away from the center plane 48. Hence, this arrangement, which does not have a zero signal variation region about the center plane 48, provides, in comparison to the first embodiment, a somewhat less desirable arrangement for detecting the passing of the moving boundary.

FIG. 3 shows another variation that has particular use in an isotachophoresis environment. In isotachophoresis, each liquid zone passes the same current; however, due to their successive higher resistivities, their temperatures are progressively higher. Consequently, a second capillary tube 60 is coaxially disposed inside of the first capillary tube 40 and carries a cooling fluid. The space 62 between the tubes 40 and 60 carries the electrolytes and the ion sample. This modification provides good coolng and coil to liquid flux coupling. It is also contemplated that additional coils or a permeable material can be contained within the second capillary tube 60; thereby allowing for a variety of inductive coil arrangements. Except when the second tube 60 is used, a substantial portion of the heat from the passing, current carrying liquid is conducted through the capillary walls of the tube 40 to the coil turns 24. As heat is received by the wire 20, the resistance of the wire 20 increases, which appears to the detector 52 as reduced resistivity of the liquid. Consequently, this tends to cancel out to some degree the effect of the higher resistivity values of subsequent ion components. To minimize this counterbalancing effect, the coil assembly 11 can be cooled by air and liquid flows exterior to the tube 40. Also, the wire 20 is chosen for low resistivity and minimum resistance temperature coefficient. In general, it is desirable to construct the entire coil assembly 11 with materials of high thermal conductivity. Moreover, the individual coils can be separated by wafers of such materials. As previously described, the capillary tube 60 can be included to minimize heat transfer to the coil turns 24.

The inductance detector 10, as described up to this point, has been in the context of its application to an isotachophoresis environment, for which it is well suited. However, the inductance detector 10 can be used for a broad range of applications wherein there is relative motion between the coil assembly 11 and a boundary between two adjoining substances of different impedances whether solids, liquids, gases or some combination thereof. The relative motion can be provided by the moving boundary and the stationary coil assembly 11, as exists in the previously described isotachophoresis application, or by having a stationary boundary and a moving coil assembly. Although not particularily desirable, the required relative motion can be generated by having the coil assembly 11 and the boundary move at different rates of speed or different directions. Consequently, in the case of adjoining liquids, the liquids can be static or flowing. Moreover, for liquids and gases the form and shape of the confinement or container thereof can vary and is not limited to the capillary tube 40 previously described. Hence, the container need not be of any particular cross section and can be closed or open, such as an open V-shaped trough.

A sampling of some illustrative applications of the inductance detector 10 to the other art areas will be provided. The inductance detector 10 can be used in liquid chromatography to determine the position of relatively diffused boundaries between adjoining liquids. In all cases, the boundary is sensed inductively. In each case the coil assembly 10 may be wound, shaped, arranged and/or excited so as to increase the sensitivity to the boundary by narrowing the sensing zone.

Figure 4:
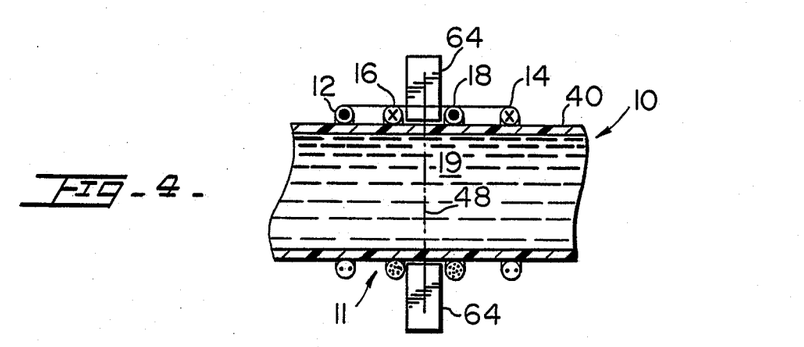
FIG. 4 shows a second detector used in combination with the inductance detector.

FIG. 4 shows modification to the embodiment of FIG. 1 wherein another detector 64, which is schematically shown, is aligned with the center of the gap between the coils 16 and 18 on the center plane 48. The detector 64 can be one of several devices, but in each case the signal generated by the detector 64 would be synchronous with the signal generated by the inductance detector 10. The detector 64, as one possibility, can comprise yet another coil which serves as a differential detector. This coil's output would peak as a boundary passed. Additionally, the detector could comprise a capacitor. Also, the detector 64 can be a conventional optical system having an illuminating source and a light detector, for detecting variations in fluorescence, refractive index and absorption. The detector 64 can be used to gate an electronic counter (not shown) for determining the time duration, for example, between adjacent boundaries. In this case, the detection 64 provides quantity measurements, while the inductance detector 10 provides sample identification information.

Heretofore, the voltage source 22 has been described as providing a current with a relatively fixed frequency. However, swept-frequency measurements, wherein the impedance of the coil assembly 11 is measured as a function of frequency, can provide valuable data.

Figure 5:
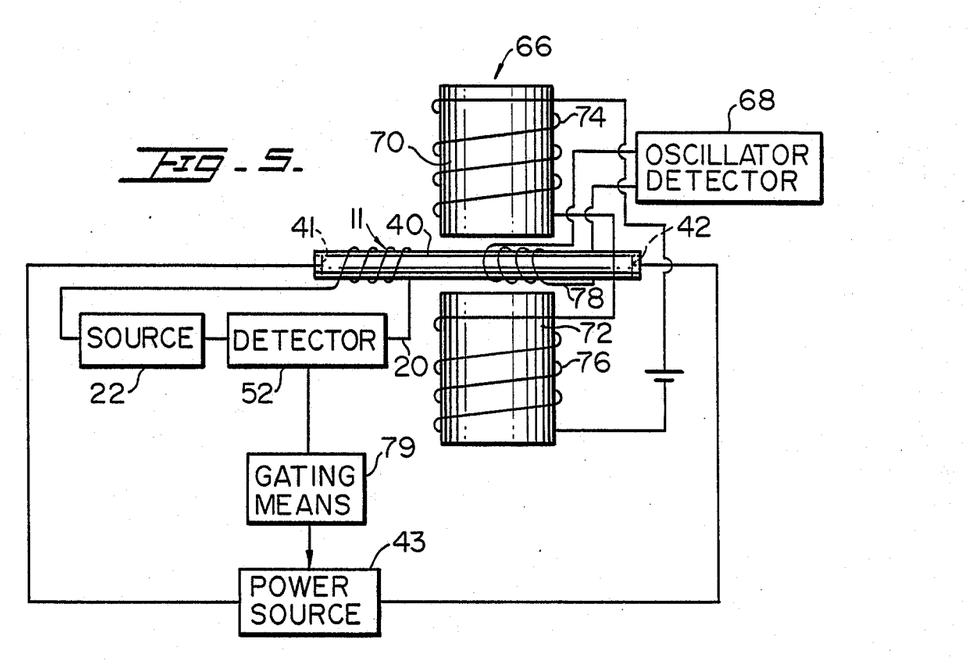
FIG. 5 shows a magnetic detector arrangement used in combination with the inductance detector.

Referring to FIG. 5, a conventional magnetic detector arrangement 66 is shown for detecting ferromagnetic, paramagnetic and/or diamagnetic properties of an ion sample in an isotachophoresis environment. The magnetic detector arrangement 66 comprises a sensitive oscillator-detector circuit 68 of a conventional design and of the type normally used in nuclear magnetic or electron paramagnetic resonance instruments. The magnetic detector arrangement 66 further comprises a pair of spaced-apart iron cores 70 and 72 having coil turns 74 and 76, respectively, which are energized by a D.C. voltage source 77 so as to apply a uniform magnetic field to the sample fluid flowing in the capillary tube 40. A R.F. coil 78 is electrically coupled to the oscillator detector circuit 68 for generating a radio frequency (R.F.) magnetic field. The magnetic properties of the fluid sample create reactance signal variations, in addition to the reactance signal variations caused by a conductivity change. The reactance changes can be detected in a known manner with the above described circuitry by recording changes in phase and frequency.

In FIG. 5, the inductance detector 10 is implemented in combination with the magnetic detector arrangement 66 and is used to provide a gating signal to stop and start the flow of ions. Hence, the coils 74 and 76 are energized by a D.C. current, the coil 78 is energized with an R.F. current and the coil assembly 11, which can include one or more coils, is energized with a current having A.C. frequencies. Gating means 79 is provided for switching off the displacement electrophoresis current, so as to halt the sample zone movement and allow the measurements of the magnetic detector arrangement 66 to be undertaken. More specifically, when the detector 52 determines that a boundary, and therefore that a given ion zone is in a desired predetermined position, such as inbetween the iron cores 70 and 72, then the detector 52 sends a signal to the gating means 79 to switch off and then subsequently, after a predetermined time period, switch on the power source 43. By sweeping either the uniform magnetic field or the R.F. field of the arrangement 66, both resistive and reactive responses are obtainable. These responses not only provide information concerning boundary movement, but also the responses are characteristic of the sample materials for identifying, for example in isotachophoresis, the zone being measured. One particularly useful application of this arrangement is for the characterization of hemoglobins.

Although the coil assembly 11 is shown in FIG. 5 as having only one coil, it can take the form of any of the multiple coil arrangements previously described. Moreover, even though the coil assembly 11 is shown displaced from the R.F. coil 78 in FIG. 5, the two can be merged into a single coil arrangement for simultaneous detection so that the single coil or coils of the coil assembly 11 are positioned between the two iron cores 70 and 72. Also, when the coil assembly 11 has even numbers of coils, such as in FIG. 1, the iron cores 70 and 72 can be placed at the center of the assembly 11. The inductance detector 10, as embodied in FIG. 5, allows a fluid flow having detectable boundaries to pass through the conventional arrangement 66 and to stop at appropriate places for detection. Hence, this arrangement 66 is readily adaptable to the isotachophoresis environment. Heretofore in prior art practices, a fluid flow, such as the ion flow of isotachophoresis, could not be passed through and analyzed by the arrangement 66. This is due to the time required for the arrangement 66 to measure the magnetic properties of the fluid positioned between the iron cores 70 and 72. However, the embodiment of FIG. 5 stops the fluid flow for a sufficient time duration in suitable positions to allow such measurements.

Figure 6:
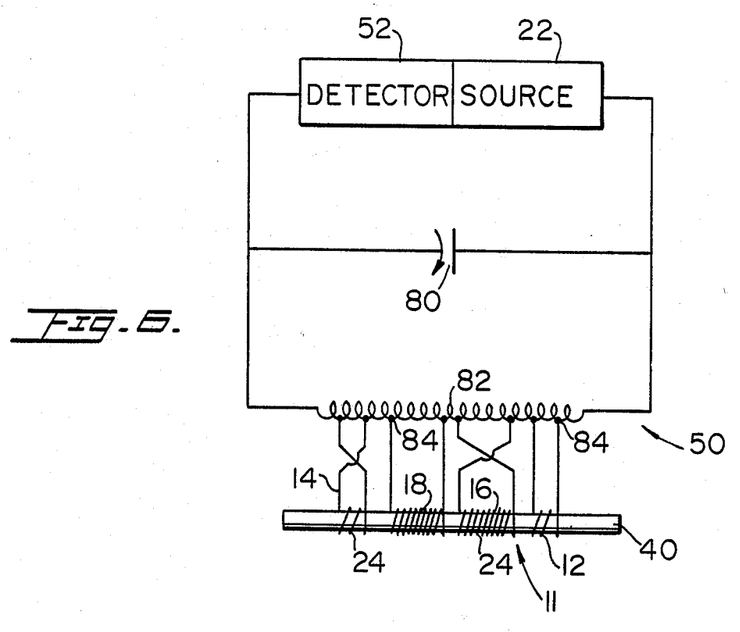
FIG. 6 is an electrical schematic of one illustrative connecting circuit for the inductance detector.

In addition to the connecting circuit 50 of FIG. 1, there are numerous other connecting circuits 50 which can be used to couple the detector 52 and the source 22 to the coil assembly 11. One such illustrative connecting circuit 50 is illustrated in FIG. 6, wherein a variable capacitor 80 is connected in parallel with the detector 52/source 22 and an inductance element 82. Each of the coils 12, 16, 18, 14 of the coil assembly 11 are electrically coupled by a pair of connector taps 84 to the inductance element 82. The respective polarities of the coils can be achieved in at least two ways. In FIG. 6, all the coil turns 24 are wound in the same direction and the currents are reversed by crossing over the connector taps 84 for each successive coil, thereby generating currents of opposite polarities. Alternatively, the currents could be in the same direction and the coil turns 24 of each successive coil could be wound in the opposite direction with respect to the previous coil. The positioning of the connector taps 84 allows for the selection of the desired current for each individual coil.

The connecting circuit 50 of FIG. 6 is shown to illustrate one exemplary circuit arrangement wherein successive reversals of current flows between subsequent coils, in contrast to reversals in the winding of coil turns, can be employed to obtain the desired magnetic fields. There are numerous other such circuits 50 which will be obvious to those skilled in the art. For instance, each coil 12, 16, 18, and 14 could be electrically coupled to the source 22 and detector 52 in a simple parallel arrangement. Also, in FIG. 6 capacitors could be placed between the connector taps 84 for each of the coils, instead of using the inductance element 82, with the capacitor 80 being replaced with an inductor. In general, this variation and the one shown in FIG. 6 will permit impedance matching to lines and/or oscillator circuit characteristics. Also, the coils 12 and 14 can be shorted, i.e., eliminating the electrical coupling to the source 22, with the coils 16 and 18 inducing a back EMF in the coils 12 and 14, so as to truncate the far ends of the sensing zones of the coil assembly 11. With reference to FIG. 1, wherein the circuit 50 is a series arrangement, a pair of high voltage capacitors (not shown) can be optionally coupled in series, one on either side of the coil assembly 11, for providing protection against possible high voltage breakdown through the wall of the capillary tube 40.

Heretofore, tthe inductance detector 10 has been illustrated and described in the context of being utilized to detect boundaries between two adjoining moving fluids, such as in isotachophoresis. However, the inductance detector 10 is useful in detecting particles suspended in a fluid, where the particles have different electrical characteristics from the suspending fluid and there is relative movement between the inductance detector 10 and the particles. In this case, the boundary being detected is the interface between the particle and the suspending fluid, i.e., the surface of the particle. This differs somewhat from the tube-traversing boundaries commonly detected between adjoining liquids in isotachophoresis.

Additionally, the inductance detector 10 is not limited to detecting individual particles, but could be used, for example, to detect agglomerates of particles. The particles could pass through a tube like the capillary tube 40 of FIG. 1. Also, the coil assembly 11 can take numerous forms and is not limited to the four coil arrangement illustrated in FIG. 1.

With the adjoining substances discussed, the primary differing characteristic has been their respective conductivities, which results in variations of the impedance of the coil assembly 11. However, differences in dielectric constants and permeability of the substances can also add to the variations in the detected coil impedance of the coil assembly 11. Since the coil turns 24 of the coils assembly 11 are at different voltages, an electric field will extend between the coils, a portion of which will extend into the capillary tube 40 and causes some dielectric effects to influence the detected coil impedance. Variations in permeability, which normally are insignificant or nonexistent, in turn can effect the impedance of the coil assembly 11 if there are significant differences thereof. Depending upon the substances being examined, and the detector circuitry the resulting frequency shifts can provide meaningful identifying information.

Figure 7:
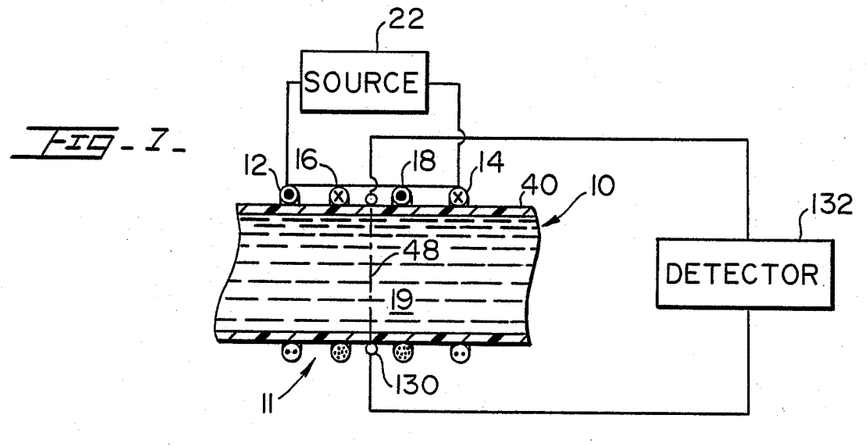
FIG. 7 is an alternative arrangement for the inductance detector as implemented in FIG. 1.

Referring to FIG. 7, an alternative differential means of detecting a moving boundary between two adjoining substances of different impedances, passing through the ambit of the coil assembly 11, is shown. A detector coil 130 is positioned between the inner coils 16 and 18, preferably in the proximity of plane 48. The coil 130 preferably has two or more coil turns and is electrically coupled to a detector 132 of conventional design. In plane 48, the primary magnetic fields generated by the coils 16 and 18 substantially cancel each other. Moreover, the concentric eddy currents generated in the sample flow create a pair of opposed secondary magnetic fields which likewise are of substantially zero magnetic field intensity in the plane 48, when there is a material of uniform conductivity throughout the inner confines of the coil assembly 11. Changes in detected impedance by the detector 132 will be primarily a function of changes in induced voltage created by a passing boundary.

Although in each of the embodiments the preferred energizing source 22 was described as providing an A.C. current, it should be understood that any periodic current source can be used wherein the waveforms of any shape vary in frequency, phase and amplitude.

Although particular embodiments of the invention have been shown and described here, there is no intention to thereby limit the invention to the details of such embodiments. On the contrary, the intention is to cover all modifications, alternatives, embodiments, usages, and equivalents of the subject invention as fall within the spirit and scope of the invention, specification and the appended claims.

What is claimed is:

1. An isotachophoresis analyzer for detecting at least one boundary between at least two adjoining substances in electrolytic solution having differing conductivity characteristics confined by a vessel, comprising:
a coil assembly, surrounding said vessel, for generating a limited magnetic field around said coil assembly thereby inducing eddy currents within said solution, comprising at least two coils, each of said two coils having at least one coil turn and wherein at least one of said two coils produces a magnetic field of opposite polarity at the far ends of the coil assembly to at least reduce one of the far ends of the magnetic field generated by said other of said two coils in its axial direction to thereby generate said limited magnetic field;
means for providing relative movement between said coil assembly and said adjoining substances so that said adjoining substances and said boundary pass into the ambit of said magnetic field generated by said coil assembly, said means including,
potential means for providing a constant electric current through said electrolytic solution,
energizing means, coupled to said coil assembly, for coupling an alternating current to energize said coil assembly to generate said magnetic field around said coil assembly; and
detecting means, coupled to said coil assembly, for detecting changes in said magnetic field caused by the movement of said boundary between said adjoining substances having differing conductivity characteristics in the ambit of said coil assembly.

2. The isotachophoresis analyzer according to claim 1, wherein said coil assembly comprises:
a pair of outer coils having coil turns wound in the same direction; and
an inner coil disposed between said outer coils having coil turns wound in the opposite direction with respect to coil turns of said outer coils; and said energizing means being electrically coupled to said coil assembly to provide electrical coil currents of the same polarity for both said inner coil and said pair of outer coils;
whereby said outer coils substantially cancel or reduce the far ends of the magnetic field generated by said inner coil.

3. The isotachophoresis analyzer according to claim 2, wherein said coil assembly comprises:
a pair of outer coils having coil turns wound in the same direction;
an inner coil disposed between said outer coils, said inner coil having coil turns wound in the same direction with respect to coil turns of said outer coils; and
said energizing means being electrically coupled to said coil assembly to provide electrical coil currents of the same polarity for both of said outer coils and of the opposite polarity for said inner coil;
whereby said outer coils substantially cancel or reduce the far ends of the magnetic field generated by said inner coil.

4. The isotachophoresis analyzer according to claim 2, wherein said inner coil has a greater number of coil turns than the combined number of coil turns for both said outer coils.

5. The isotachophoresis analyzer according to claim 1, wherein said coil assembly comprises:
a pair of coils, each said coil having coil turns wound in an opposite direction with respect to the coil turns of the other coil; and
said energizing means being electrically coupled to said coil assembly to provide electrical coil currents of the same polarity for both of said pair of coils;
whereby a region of zero magnetic field intensity is provided between said coils.

6. The isotachophoresis analyzer according to claim 1, wherein said coil assembly comprises:
a pair of coils having coil turns wound in the same direction; and
said energizing means being electrically coupled to said coil assembly to provide electrical coil currents of one polarity to one of said coils and the opposite polarity to said other coil;
whereby a region of zero magnetic field intensity is provided between said coils.

7. The isotachophoresis analyzer according to claim 5, wherein each of said coils has substantially the same number of coil turns.

8. The isotachophoresis analyzer according to claim 1, wherein said coil assembly comprises,
a pair of outer coils, each said outer coil having coil turns wound in the opposite direction with respect to the coil turns of the other said outer coil;
a pair of inner coils, each said inner coil having coil turns wound in opposite direction with respect to the coil turns of the other said inner coil;
said pair of inner coils being intermediately disposed between said outer coils, each said outer coil being oppositely wound with respect to the adjacent said inner coil; and
said energizing means being electrically coupled to said coil assembly to provide coil currents of the same polarity to both said inner coils and said outer coils;
whereby a region of substantially zero magnetic field strength exists between said inner coils, and the far ends of the magnetic field generated by said inner coils are substantially cancelled or reduced by said outer coils.

9. The isotachophoresis analyzer according to claim 1, wherein said coil assembly comprises,
a pair of outer coils having coil turns wound in the same direction;
a pair of inner coils having coil turns wound in the same direction as the coil turns of said outer coils;
said pair of inner coils being intermediately disposed between said outer coils;
said energizing means being electrically coupled to said coil assembly to provide coil currents of one polarity to one of said outer coils and to the most remotely disposed coil of said pair of inner coils with respect to said one outer coil, and to provide coil currents of the opposite polarity to the other said outer coil and to the other inner coil.

10. The isotachophoresis analyzer according to claim 8, wherein each said inner coil has a greater number of coil turns than each said outer coil, said inner coils have substantially the same number of coil turns, and said outer coils have substantially the same number of coil turns.

11. The isotachophoresis analyzer according to claim 1, wherein said vessel comprises a first capillary tube.

12. The isotachophoresis analyzer according to claim 11, further including, a second capillary tube disposed in coaxial relationship inside said first capillary tube for containing a moving cooling substance, whereby heat, at least in part, is removed by said cooling substance.

13. The isotachophoresis analyzer according to claim 5, further including, detector means disposed between the said coils;

synchronous measurement means, coupled to said detector and detecting means, for providing synchronous measurements through both said detector means and said detecting means.

14. The isotachophoresis analyzer according to claim 8, further including, detector means disposed between the said inner coils;

synchronous measurement means, coupled to said detector and detecting means, for providing synchronous measurements through both said detector means and said detecting means.

15. A chromatographic analyzer for detecting at least one boundary between at least two adjoining substances in electrolytic solution having differing ionic mobilities confined by a vessel, comprising:

a coil assembly, surrounding said vessel, for generating a limited magnetic field around said coil assembly thereby inducing eddy currents within said solution, comprising at least two coils, each of said two coils having at least one turn, and wherein at least one of said two coils produces a magnetic field of opposite polarity at the far ends of the coil assembly to at least reduce one of the far ends of the magnetic field generated by said other of said two coils in its axial direction to thereby generate said limited magnetic field;

means for providing relative movement between said coil assembly and said adjoining substances so that said adjoining substances and said boundary pass into the ambit of said magnetic field generated by said coil assembly;

energizing means, coupled to said coil assembly, for coupling an alternating current to energize said coil assembly to generate said magnetic field around said coil assembly; and detecting means, coupled to said coil assembly, for detecting changes in said magnetic field caused by the movement of said boundary between said adjoining substances having differing ionic mobilities in the ambit of said coil assembly.

16. The analyzer according to claim 15, wherein said coil assembly comprises:

a pair of outer coils having coil turns wound in the same direction; and an inner coil disposed between said outer coils having coil turns wound in the opposite direction with respect to coil turns of said outer coils; and said energizing means being electrically coupled to said coil assembly to provide electrical coil currents of the same polarity for both said inner coil and said pair of outer coils;

whereby said outer coils substantially cancel or reduce the far ends of the magnetic field generated by said inner coil.

17. The analyzer according to claim 15, wherein said coil assembly comprises:

a pair of outer coils having coil turns wound in the same direction;

an inner coil disposed between said outer coils, said inner coil having coil turns wound in the same direction with respect to coil turns of said outer coils; and said energizing means being electrically coupled to said coil assembly to provide electrical coil currents of the same polarity for both of said outer coils and of the opposite polarity for said inner coil;

whereby said outer coils substantially cancel or reduce the far ends of the magnetic field generated by said inner coil.

18. The analyzer according to claim 16, wherein said inner coil has a greater number of coil turns than the combined number of coil turns for both said outer coils.

19. The analyzer according to claim 15, wherein said coil assembly comprises:

a pair of coils, each said coil having coil turns wound in an opposite direction with respect to the coil turns of the other coil; and said energizing means being electrically coupled to said coil assembly to provide electrical coil currents of the same polarity for both of said pair of coils;

whereby a region of zero magnetic field intensity is provided between said coils.

20. The analyzer according to claim 15, wherein said coil assembly comprises:

a pair of coils having coil turns wound in the same direction; and said energizing means being electrically coupled to said coil assembly to provide electrical coil currents of one polarity to one of said coils and the opposite polarity to said other coil;

whereby a region of zero magnetic field intensity is provided between said coils.

21. The analyzer according to claim 19, wherein each of said coils has substantially the same number of coil turns.

22. The analyzer according to claim 15, wherein said coil assembly comprises, a pair of outer coils, each said outer coil having coil turns wound in the opposite direction with respect to the coil turns of the other said outer coil;

a pair of inner coils, each said inner coil having coil turns wound in opposite direction with respect to the coil turns of the other said inner coil;

said pair of inner coils being intermediately disposed between said outer coils, each said outer coil being oppositely wound with respect to the adjacent said inner coil; and said energizing means being electrically coupled to said coil assembly to provide coil currents of the same polarity to both said inner coils and said outer coils;

whereby a region of substantially zero magnetic field strength exists between said inner coils, and the far ends of the magnetic field generated by said inner coils are substantially cancelled or reduced by said outer coils.

23. The analyzer according to claim 15, wherein said coil assembly comprises, a pair of outer coils having coil turns wound in the same direction;

a pair of inner coils having coil turns wound in the same direction as the coil turns of said outer coils;

said pair of inner coils being intermediately disposed between said outer coils;

said energizing means being electrically coupled to said coil assembly to provide coil currents of one polarity to one of said outer coils and to the most remotely disposed coil of said pair of inner coils with respect to said one outer coil, and to provide coil currents of the opposite polarity to the other said outer coil and to the other inner coil.

24. The analyzer according to claim 22, wherein each said inner coil has a greater number of coil turns than each said outer coil, said inner coils have substantially the same number of coil turns, and said outer coils have substantially the same number of coil turns.

25. The analyzer according to claim 15, wherein said vessel comprises a first capillary tube.

26. The analyzer according to claim 25, further including, a second capillary tube disposed in coaxial relationship inside said first capillary tube for containing a moving cooling substance, whereby heat, at least in part, is removed by said cooling substance.

27. The analyzer according to claim 19, further including, detector means disposed between the said coils;

synchronous measurement means, coupled to said detector and detecting means, for providing synchronous measurements through both said detector means and said detecting means.

28. The analyzer according to claim 22, further including, detector means disposed between the said inner coils;

synchronous measurement means, coupled to said detector and detecting means, for providing synchronous measurements through both said detector means and said detecting means.

29. A method of detecting at least one boundary formed between at least two adjoining liquid substances having differing ionic mobilities resulting from the introduction of at least one sample of liquid substance into a solution confined by a vessel in a chromatographic analyzer, comprising the steps of:

generating a limited magnetic field in the ambit of said solution to thereby induce eddy currents within said solution by generating a first magnetic field having far axial ends and generating at least one second magnetic field to cancel at least one of said far axial ends of the first magnetic field to thereby reduce at least one of said far axial ends of said first magnetic field;

providing relative motion between the adjoining substances and the limited magnetic field so that the boundary formed between said two substances moves into said generated limited magnetic field; and detecting changes in said limited magnetic field caused by the movement of said boundary between said adjoining substances having differing ionic mobilities into the ambit of said limited magnetic field.

30. A method of detecting at least one boundary formed between at least two adjoining liquid substances having differing conductivity characteristics resulting from the introduction of at least one sample of liquid substance into an electrolytic solution comprising a leading electrolyte and a terminal electrolyte confined by a vessel having a constant current applied through said electrolyte solution in a isotachophoresis analyzer, comprising the steps of:

maintaining said current constant;

generating a limited magnetic field in the ambit of said electrolytic solution to thereby induce eddy currents within said solution by generating a first magnetic field having far axial ends and generating at least one second magnetic field to cancel at least one of said far axial ends of the first magnetic field to thereby reduce at least one of said far axial ends of said first magnetic field;

providing relative motion between the adjoining substances and the limited magnetic field so that the boundary formed between said two substances moves into said generated limited magnetic field; and detecting changes in said limited magnetic field caused by the movement of said boundary between said adjoining substances having differing conductivities into the ambit of said limited magnetic field.

31. A method of detecting at least one boundary formed between at least two adjoining liquid substances in solution having differing ionic mobilities resulting from the introduction of at least one sample of liquid substance into an electrolytic solution comprising an electrolyte confined by a vessel having a d.c. current applied through said electrolyte, comprising the steps of:

generating a limited magnetic field in the ambit of said electrolytic solution to thereby induce eddy currents within said solution by generating a first magnetic field having far axial ends and generating at least one second magnetic field to cancel at least one of said far axial ends of the first magnetic field to thereby reduce at least one of said far axial ends of said first magnetic field;

providing relative motion between the adjoining substances and the limited magnetic field so that the boundary formed between said two substances moves into said generated limited magnetic field; and detecting changes in said limited magnetic field caused by the movement of said boundary between said adjoining substances having differing ionic mobilities into the ambit of said limited magnetic field.

32. The method according to claim 31 wherein said limited magnetic field in generated around said electrolytic solution.

* * * * *